United States Patent [19]

DeLuca et al.

[11] Patent Number: 4,755,329

[45] Date of Patent: Jul. 5, 1988

[54] PROCESS AND INTERMEDIATES FOR PREPARING 1α-HYDROXYVITAMIN D COMPOUNDS

[75] Inventors: Hector F. DeLuca; Heinrich K. Schnoes, both of Madison, Wis.; Seok H. Lee, Brighton, Mass.

[73] Assignee: Wisconsin Alumni Research Foundation, Madison, Wis.

[21] Appl. No.: 743,129

[22] Filed: Jun. 10, 1985

[51] Int. Cl.⁴ .................... C07J 9/00; C07C 85/11; C07C 35/08
[52] U.S. Cl. .................... 260/397.2; 568/420; 568/828
[58] Field of Search .................... 260/397.2; 568/420, 568/700, 828

[56] References Cited

U.S. PATENT DOCUMENTS 4,594,340  6/1986  Partridge et al. ............... 260/397.2
4,594,432  6/1986  Baggiolini et al. ............. 260/397.2

OTHER PUBLICATIONS

Chemical Abstracts; vol. 98, #216562k (1982); Baggiolini et al.
Chemical Abstracts; vol. 97; #24084s (1982); Baggiolini et al.

*Primary Examiner*—Leonard Schenkman
*Assistant Examiner*—Joseph A. Lipovsky
*Attorney, Agent, or Firm*—Howard W. Bremer

[57] ABSTRACT

The invention relates to ring A-diol units suitable for synthesizing 1α-hydroxyvitamin D compounds by subsequent condensation with appropriate $C/D$-ring fragments and to methods for preparing such ring A-diol units.

7 Claims, No Drawings

PROCESS AND INTERMEDIATES FOR PREPARING 1α-HYDROXYVITAMIN D COMPOUNDS

This invention was made Government support under NIH Grant No. AM-14881 awarded by the Department of Health and Human Services. The Government has certain rights to this invention.

TECHNICAL FIELD

This invention relates to the synthesis of 1α-hydroxyvitamin D compounds. More specifically, this invention relates to a process for generating key intermediates for the preparation of 1α-hydroxyvitamin D compounds.

BACKGROUND ART

For the control of calcium metabolism in animals and humans, and the maintenance of the physiological calcium balance, 1α-hydroxylated vitamin D metabolites are well-known regulatory agents. Particularly important in this regard is 1α,25-dihydroxyvitamin $D_3$ (1,25-$(OH)_2D_3$), the natural hormonal form for the maintenance of calcium homeostastis in vivo, but a variety of other 1α-hydroxyvitamin D derivatives (e.g. 1α-hydroxyvitamin $D_3$, 1α-hydroxyvitamin $D_2$, 1α,25-dihydroxyvitamin $D_2$), and certain fluorinated analogs, also exhibit potent calcemic activity. All of these compounds are of great practical importance as therapeutic agents for the treatment of a variety of calcium balance disorders, e.g. rickets, osteomalacia, osteoporosis, renal osteodystrophy and others. As a consequence, there has been much interest in the chemical synthesis of both the natural 1α-hydroxyvitamin D compounds and their structural analogs and the literature contains many examples of useful synthetic procedures. Summaries of the known methods are presented in several reviews, e.g. DeLuca et al. Topics Current Chem. 83, 1-65 (1979); Yakhimovich, Russ. Chem. Rev. 49, 371-83 (1980); or Jones and Rasmusson, Progress Chem. Org. Nat. Products, vol. 39, 64-121 (1980). In general, the known methods of synthesis of 1α-hydroxyvitamin D compounds are of three types, namely (a) synthesis from a suitable steroid precursor, (b) synthesis from a vitamin D precursor, i.e. by direct hydroxylation at carbon 1, and (c) total synthesis of the desired vitamin D compound from simple precursors, generally involving the coupling of a unit representing ring-A of the desired vitamin to a suitable partner representing the C/D-ring portion so as to generate the complete vitamin D structure and characteristic triene chromophore. Exemplary of this last approach, and especially relevant to the present invention, is the report by Baggiolini et al. [J. Am. Chem. Soc. 104, 2945-48 (1982)], describing the synthesis of 1α,25-dinydroxyvitamin $D_3$. In this case, the protected alcohol of structure A below (representing ring-A of the vitamin molecule) is initially prepared and is then, after conversion to the Wittig reagent B, condensed with the separately synthesized ketone C (where in this case, R represents the side-chain of 25-hydroxycholesterol) to obtain the 1α,25-$(OH)_2D_3$-derivative. The crucial ring A-1,3-diol unit (structure A, below) is synthesized from the monoterpene d-carvone in a procedure involving twelve synthetic steps.

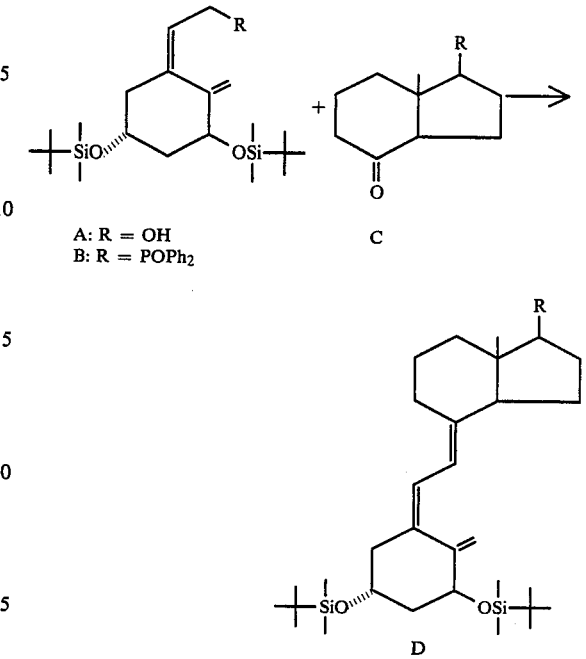

A: R = OH
B: R = $POPh_2$
C

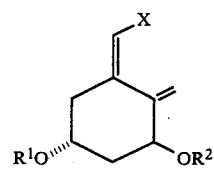

D

DISCLOSURE OF INVENTION

A new method for preparing of ring A-diol units suitable for the synthesis of 1α-hydroxyvitamin D compounds has been developed. In its preferred embodiment, the method specifically provides the ring A-1,3-diol unit having the general structure shown below:

where each of $R^1$ and $R^2$ represent hydrogen or a hydroxy-protecting group, and where X is a hydroxymethyl (—$CH_2OH$) or a carboxaldehyde (—CHO) group.

1α-Hydroxy-ring-A units, where X is a hydroxyethyl group can be used for a synthesis of any desired 1α-hydroxyvitamin D compounds, by condensation with the appropriate C/D-ring fragment as demonstrated by Baggiolini et al. (supra).

The corresponding aldehydic 1α-hydroxy-ring-A units shown above (X=CHO) are useful either as intermediates to the alcohol (X=$CH_2OH$), but they can also be used as such for the synthesis of 1α-hydroxyvitamin D derivatives, namely by direct condensation with a suitable partner (i.e. by Wittig, Grignard or aldol-type reactions) so as to obtain a desired 1α-hydroxyvitamin D compound, or 1α-hydroxyvitamin D analog.

The term "hydroxy-protecting" group as used in this description or in the claims, signifies any group commonly used for the temporary protection of hydroxy functions. Such groups are, for example, acyl groups of 1-5 carbons, in all isomeric forms, or aroyl groups, such as benzoyl or halo, nitro- or alkyl-substituted benzoyl groups, or alkylsilyl groups (such as trimethylsilyl, triethylsilyl, t-butyldimethylsilyl, etc.) or ether-protecting groups such as tetrahydropyranyl, tetrahydrofuranyl, methoxymethyl, methoxyethyl, methoxyethoxymethyl and related groups. A "protected hydroxy" group, therefore, is a hydroxy function derivatized with one of these protecting groups. An "alkyl" group is a hydrocarbon radical of 1 to 5 carbons in all isomeric forms.

The preparation of the above-shown ring A-synthons comprises the steps shown in Process Scheme I. The starting material is a 1α-hydroxyvitamin D compound, represented by the general structure $\underline{1}$ in Process Scheme I, where each of $R^1$ and $R^2$ represent hydrogen or a hydroxy-protecting group and where R can be any compatible side-chain group, which may, for example, have the general structure shown below:

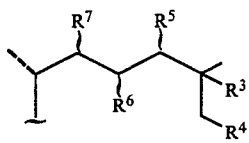

wherein $R^3$ and $R^4$, independently represent hydrogen, hydroxy or a protected hydroxy group, where $R^5$ represents hydrogen, hydroxy, protected hydroxy or an alkyl group, and where $R^6$ and $R^7$ represent hydrogen, hydroxy, protected hydroxy or, taken together, form a carbon-carbon bond.

Preferred starting materials are 1α-hydroxyvitamin $D_3$ or 1α-hydroxyvitamin $D_2$ or their hydroxy-protected derivatives. These starting material are readily available by known processes.

In the first step of the process, the starting material of structure $\underline{1}$ is dihydroxylated at carbons 7 and 8 to obtain the 7,8-diol derivative $\underline{2}$ (see Process Scheme I), where R, $R^1$ and $R^2$ have the meaning as defined above. A suitable oxidant for the introduction of the hydroxy groups is osmium tetroxide. This reaction is conducted in an organic solvent, and at a temperature of from ca. 0° C. to about 50° C. Under such conditions the 7,8-vicinal diol $\underline{2}$ is formed as the major product and it is noteworthy that there is little or no attack by the oxidant on the other available double bonds of the triene system, e.g. the 5,6- or 10,19-double bonds. The 1α-hydroxyvitamin D 7,8-diols of general structure $\underline{2}$ are new compounds. Three vitamin D 7,8-diols, but lacking the crucial 1α-hydroxy-function, namely the 7,8-diols of vitamin $D_2$ and $D_3$ and the 7,8-diol of 25-hydroxyvitamin $D_3$ have been prepared previously (Lythgoe, Chem. Soc. Rev. 9, 449 (1980); Toh and Okamura, J. Org. Chem. 43, 1414 (1983); and DeLuca et al. U.S. Pat. No. 4,448,726).

The next step of the process comprises the cleavage of the 7,8-diol function in compound $\underline{2}$ so as to obtain the aldehyde of general structure $\underline{3}$ where $R^1$ and $R^2$ have the meaning as defined above (see Process Scheme I). The cleavage of the 7,8-diol can be accomplished with diol cleavage reagents. Effective reagents are, for example, periodate salts, or lead tetracetate. The reaction is conducted in an organic solvent (e.g. an alcoholic solvent or a hydrocarbon or ether solvent) at a temperature from about 0° C. to about 50° C. The desired aldehyde of structure $\underline{3}$ can be isolated from the reaction mixture by chromatography. Products of structure $\underline{3}$, containing the synthetically very useful, but also chemically sensitive and reactive conjugated aldehyde group, are new compounds.

As shown in the Process Scheme I, the other product resulting from 7,8-vicinal diol cleavage is the fragment corresponding to rings C and D plus side-chain of the original vitamin D-starting material. This CD-ketone, if desired, can also be isolated and purified by chromatography, but for the purposes of the present invention, the material is simply removed as a side product.

By reduction of the aldehyde of structure $\underline{3}$, there is obtained the corresponding alcohol $\underline{4}$ (Process Scheme I); this reduction is accomplished very conveniently by hydride reducing agents, e.g. $NaBH_4$, or $LiAlH_4$ or related hydride reagents well known in the art. Reduction is preferably effected in an organic solvent (e.g. an alcohol or hydrocarbon or ether solvent) at a temperature from about $-30°$ C. to the boiling temperature of the solvent. In this manner, aldehyde $\underline{3}$ is smoothly reduced to the alcohol $\underline{4}$, where $R^1$ and $R^2$ represent hydrogen or a hydroxy-protecting group.

The alcohol of structure $\underline{4}$, where $R^1$ and $R^2$ represent hydrogen or a hydroxy-protecting group can then be used (as illustrated by the report of Baggiolini et al., supra) for the synthesis of any desired 1α-hydroxyvitamin D compound by coupling this unit (e.g. via Wittig-type reactions) with a suitable partner representing rings C and D of the desired vitamin product. Likewise, as mentioned above, the aldehyde of structure $\underline{3}$, in addition to being an intermediate to alcohol $\underline{4}$, can serve directly as a building block for the ring A-unit of 1α-hydroxyvitamin D compounds, by condensing it with a suitable C/D-ring fragment, via standard and conventional coupling reactions, such as the Wittig reaction, the Grignard reaction, or by aldol condensation.

Thus, the above-described process provides a convenient method for generating a 1α-hydroxy ring A unit in the form of aldehyde $\underline{3}$ or of alcohol $\underline{4}$, and this unit can then be used as a synthetic building block for the preparation of a broad range of desirable 1α-hydroxyvitamin D metabolites and analogs according to known methods. A notable feature of the present process is that it provides either aldehyde $\underline{3}$ or alcohol $\underline{4}$. A further advantage is that the stereochemistry of all substituents in the 1α-hydroxy-ring A units of type $\underline{3}$ or $\underline{4}$ is exactly known and defined by the starting material used, and that these starting materials required for the above process are readily available, e.g. in the form of 1α-hydroxyvitamin $D_3$ or 1α-hydroxyvitamin $D_2$ or their hydroxy-protecting derivatives (i.e. the compounds represented by structure $\underline{1}$ in the process scheme, where R is the side-chain of cholesterol and ergosterol, respectively). These compounds are available and can be prepared by a variety of methods (see reviews of Jones & Rasmusson, DeLuca et al.; Yakhimovich, supra) among which the route via cyclovitamin intermediates (U.S. Pat. Nos. 4,195,027 and 4,260,549) is particularly convenient because of its efficiency and generality.

The present invention is more particularly defined by the following illustrative examples. In these examples, compounds identified by Arabic numerals, e.g. $\underline{1}$, $\underline{2}$, $\underline{3}$, $\underline{4}$, refer to the structures so numbered in Process Scheme I.

EXAMPLE 1

Preparation of Alcohol $\underline{4}$ ($R^1=R^2=$t-butyldimethylsilyl)

(a) To a solution of 1α-hydroxyvitamin $D_3$ (400 mg, 1 mmole) in 10 ml of dimethylformamide was added tert-butyldimethylsilyl chloride (362 mg, 2.4 mmole) and imidazole (340 mg, 5 mmole), and the mixture was stirred at room temperature under nitrogen until the reaction was complete (about 4 hr) as judged by thin layer chromatography (using silica gel plates and 30% ethylacetate-hexane as solvent). The mixture was then poured over ice-cold water and extracted three times with ether. The combined extracts were washed with $H_2O$ and brine, then dried over $MgSO_4$, filtered and concentrated in vacuo to give 530 mg (89% yield) of di-tert.-butyldimethylsilyl-1α-hydroxyvitamin $D_3$ (compound 1, $R^1=R^2=$tert.-butyldimethylsilyl).

(b) $OsO_4$ (255 mg, 1.0 mmole) was added to a stirred pyridine solution (10 ml) of the product (530 mg, 0.84 mmole) obtained in (a) above. The mixture was stirred at room temperature under nitrogen for 15 min, then 10% $NaHSO_3$ (10 ml) was added. The mixture was stirred further for 1 hr, diluted with 10% $NaHSO_3$ (20 ml), and extracted with ether (3×50 ml). The combined extracts were washed consecutively with $H_2O$, 1N HCl, 10% $NaHCO_3$, $H_2O$, and saturated NaCl solution, then dried over $MgSO_4$, and solvent was evaporated in vacuo to obtain the 7,8-diol product (compound 2, $R^1=R^2=$tert.-butyldimethylsilyl).

(c) Lead tetracetate ($Pb(OCOCH_3)_4$, 450 mg, 1.0 mmole) was added to a stirred solution (10 ml of benzene and 0.5 ml of pyridine) of the 7,8-diol (558 mg, 0.84 mmole) obtained in (b) above. The reaction was allowed to proceed at room temperature under nitrogen for 20 min, and was then filtered to remove the precipitate. The filter cake was washed with fresh benzene (3×2 ml).

The combined filtrate which contains the aldehyde 3 ($R^1=R^2=t=$butyldimethylsilyl) was cooled to 0° C. on an ice bath and Red-Al (70% solution of sodium bis(2-methoxyethoxy)aluminum hydride in toluene; 1 ml) was added under nitrogen. The mixture was stirred for 2 hr, water was added dropwise until grayish precipitates formed, and the precipitates were removed by filtration. The filter cake was washed with fresh ether (3×10 ml). The combined filtrates were washed with water (1×10 ml), saturated NaCl (2×10 ml), then dried over anhydrous $MgSO_4$, filtered, and concentrated in vacuo. Column chromatography on silica gel (2 cm×25 cm, eluted with 10% ethyl acetate-hexane, 500 ml, and 20% ethyl acetate-hexane, 500 ml was carried out to provide 99 mg of alcohol 4 ($R^1=R^2=$tert.-butyldimethylsilyl). Further purification was achieved by preparative TLC using 10% ethyl acetate-hexane (multiple elution). The product (compound 4, where $R^1=R^2=$tert.-butyldimethylsilyl) showed UV ($C_2H_5OH$) $\lambda_{max}$ 218 nm; mass spectrum, m/z (relative intensity) 398 ($M^+$, 0,1), 380 (0.8), 367 (0.7), 341 (4), 323 (1), 209 (27), 117 (12), 91 (9), 75 (100); $^1$H-NMR ($CDCl_3$) δ 0.06 (s, $Si(CH_3)_2$), 0.87 and 0.90 (s, Si-C$(CH_3)_3$), 1.83 (2H, triplet pattern, J~6 Hz, C-2-Hz), 2.20 (1H, dd, J=14 and 6 Hz, C-4-H), 2.41 (1H, dd, J=14 and 2.5 Hz, C-4-H), 4.18 (3H, m, appears as triplet, J~6 Hz, C-7-H$_2$ and C-3-H), 4.41 (1H, triplet pattern, J~6 Hz, C-1-H), 4.77 and 5.16 (1H each, br. s, C-19-H$_2$), 5.53 (1H, triplet pattern, J~6 Hz, C-6-H).

EXAMPLE 2

Preparation of Aldehyde 3 and Alcohol 4 ($R^1=R^2=COCH_3$)

(a) 1α-Hydroxyvitamin $D_3$ (170 mg, 0.425 mmole) in pyridine (0.4 ml) containing acetic anhydride (0.2 ml) was heated at 50° for 2 hr under nitrogen. The mixture was cautiously neutralized over ice-saturated $NaHCO_3$ and extracted with ether (3×30 ml). The combined extracts were washed with water (1×15 ml), saturated NaCl (2×15 ml), then dried over anhydrous $MgSO_4$, filtered, and concentrated in vacuo to give 210 mg of the diacetate (compound 1, $R^1=R^2=$Ac).

(b) Osmium tetroxide (125 μl, 10% solution in pyridine) was added to a stirred solution of the diacetae (23 mg, 0.044 mmole) in pyridine (0.5 ml). The reaction was allowed to proceed at room temperature under nitrogen for 15 min. 10% $NaHSO_3$ (0.5 ml) was added, the mixture was stirred further for 30 min, then diluted with 10% $NaHSO_3$ (5 ml), and extracted with ether (3×15 ml). The combined extracts were washed with water (2×10 ml), saturated NaCl (2×10 ml), then dried over anhydrous $MgSO_4$, filtered, and concentrated in vacuo. Chromatography on silica gel using 5% methanol-chloroform provided 12 mg of 7,8-diol (compound 2, $R^1=R^2=$Ac); mass spectrum, m/z (relative intensity), 518 ($M^+$), 500 (0.2), 482 (0.4), 440 (0.8), 422 (2), 380 (43), 249 (19), 247 (26), 134 (100), 105 (43); NMR ($CDCl_3$) δ 0.75 (s, C-18-H$_3$), 2.02 (s, 3-OCOCH$_3$), 2.05 (s, C-1-OCOCH$_3$), 4.73 (dd, J=9.6 Hz, 5.6 Hz, C-7-H), 5.12 (septet, C-1-H), 5.33 (br, s, 19Z-H), 5.40 (br, s, 19E-H), 5.53 (t(sharp), C-3-H), 5.81 (d, J=9.6 Hz, C-6-H).

(c) Saturated aqueous $NaIO_4$ (0.1 ml) was added to a stirred solution of the 7,8-diol (10 mg) in methanol (0.3 ml) and the mixture was heated at 50° under nitrogen for 2.5 hr. Ice-cold water (5 ml) was added, the mixture was extracted with ether (3×10 ml), and the combined extracts were washed with water (2×5 ml), saturated NaCl (1×5 ml), then dried over anhydrous $MgSO_4$, filtered and concentrated in vacuo. From the residue, the aldehyde of structure 3 ($R^1=R^2=$Ac) can be isolated by HPLC (silica gel column, 5–10% ethyl acetate in hexane as eluent).

Alternatively, the crude aldehyde 3, obtained after the vicinal diol cleavage reaction, is reduced with $NaBH_4$ (in ether/methanol, 0.5 ml) and the resulting reduction product is purified on HPLC (Zorbax-Sil semipreparative column) using 10% isopropanol-hexane as eluent to obtain alcohol 4 ($R^1=R^2=COCH_3$).

EXAMPLE 3

Preparation of Aldehyde 3 and Alcohol 4 ($R^1=R^2=$t-butyldimethylsilyl)

(a) tert-Butyldimethylsilyl chloride (46 mg, 0.30 mmole) and imidazole (43 mg, 0.625 mmole) was added to a solution of 1α-hydroxyvitamin $D_3$ (50 mg, 0.125 mmole) in DMF (5 ml), and the mixture was stirred at room temperature under nitrogen for 3 hr (or until the reaction was complete, judged by TLC using 30% ethyl acetate-hexane). The mixture was then poured over ice-cold water and extracted three times with ether (3×25 ml). The combined extracts were washed with water (1×15 ml) and saturated aqueous sodium chloride, dried over anhydrous magnesium sulfate, filtered, and concentrated in vacuo to give the product (compound 1, $R^1=R^2=$tert.-butyldimethylsilyl). (Rf 0.69 on silica gel in 30% ethyl acetate-hexane): UV ($C_2H_5OH$) $\lambda_{max}$ 216 nm.

(b) Osmium tetroxide ($OsO_4$; 39 mg, 0.15 mmole) was added to a solution of di-tert.-butyldimethylsilyl-1α-hydroxyvitamin (78 mg, 0.125 mmole, theoretical) in pyridine (3 ml). The mixture was stirred at room temperature under nitrogen for 15 min, then 10% $NaHSO_3$ (5 ml) was added to quench the reaction. The mixture was stirred further for 1 hr, diluted with 10% $NaHSO_3$ (10 ml); and extracted with ether (3×30 ml). The combined extracts were washed with water (2×15 ml), 1N HCl (2×15 ml), 10% NaHCO₃ (2×15 ml), water (1×15 ml), and saturated NaCl, then dried over anhydrous MgSO₄, filtered, and concentrated in vacuo, to obtain the 7,8-diol (2), $R^1=R^2=$ tert.-butyldimethylsilyl).

(c) Lead tetracetate (67 mg, 0.15 mmole) was added to a stirred solution of the 7,8-diol (2) (82 mg, 0.125 mmole) in benzene (2 ml) containing pyridine (0.2 ml). The reaction was allowed to proceed at room temperature under nitrogen for 15 min, the mixture was then poured over ice-cold water (15 ml) and extracted with ether (3×30 ml), and the combined extracts were washed with water (1×15 ml) and saturated NaCl (2×15 ml), then dried over anhydrous MgSO₄, filtered, and concentrated in vacuo. Thin layer chromatography on silica gel using 15% ethyl acetate-hexane as eluent (triple elution) provided the aldehyde 3 ($R^1=R^2=$ tert.-butyldimethylsilyl) (6.6 mg; Rf 0.58 on silica gel in 30% ethyl acetate-hexane) in 13% yield: UV ($C_2H_5OH$) $\lambda_{max}$ 248 nm, $\lambda_{min}$ 218 nm; mass spectrum: m/z (relative intensity) 396 (M⁺, 2) 381 (1), 339 (18), 264 (37), 207 (23), 181 (35), 133 (15), 101 (14), 75 (100), 57 (21). ¹H NMR (CDCl₃) δ 0.07 and 0.08 (s, Si-(CH₃)₂), 0.88 and 0.9 (s, Si-C(CH₃)₃), 1.88 and 1.96 (m, C-2-H₂), 2.42 (1H, dd, J=14 and 6 Hz, C-4-H), 2.59 (1H, dd, J=14 and 2 Hz, C-4-H), 4.32 (m, C-3-H), 4.58 (m, C-1-H), 5.08 and 5.43 (brs, C-19-H₂), 5.96 (d, J=7.5 Hz, C-6-H), 9.80 (d, J=7.5 Hz, C-7-H).

(d) The aldehyde (3) as obtained in (c) above, when reduced with bis(2-methoxyethoxy)aluminum hydride as described in Example 1(c) above, gave the corresponding allylic alcohol 4 ($R^1=R^2=$ tert.-butyldimethylsilyl).

EXAMPLE 4

Preparation of 1α,7,8-Trihydroxy-7,8-Dihyxdrovitamin D₃ (Compound 2, $R^1=R^2=H$)

Osmium tetroxide treatment of 1α-hydroxyvitamin D₃ using the conditions described in Example 1(b) above gave the corresponding 7,8-diol 2 ($R^1=R^2=H$). The compound was purified by HPLC (Zorbax-Sil semipreparative column) using 10% isopropanol-hexane. UV ($C_2H_5OH$) $\lambda_{max}$ 216 nm; mass spectrum: m/z (relative intensity) 434 (M⁺), 416 (2), 398 (9), 380 (31), 362 (3), 265 (15), 247 (44), 221 (6), 152 (52), 135 (56), 125 (22).

Process Schematic I

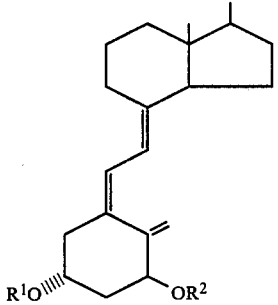

Process Schematic I -continued

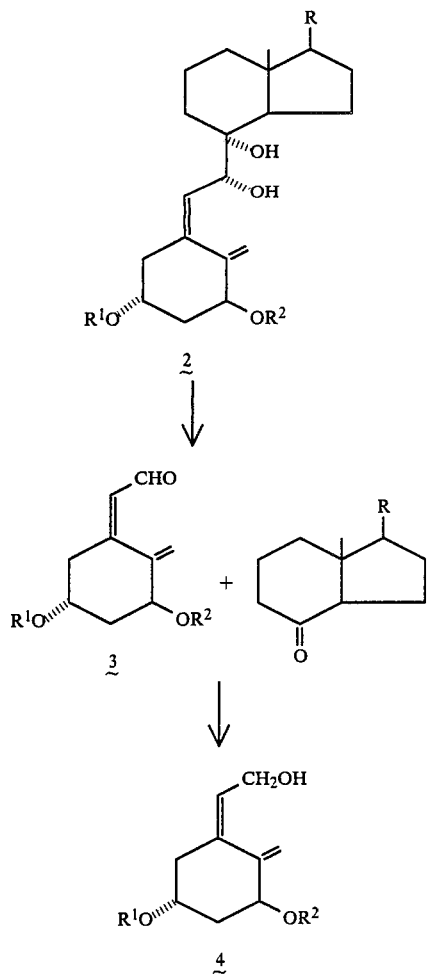

We claim:

1. A compound having the formula

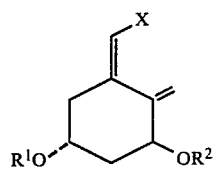

where X is a carboxyaldehyde (—CHO) group and each of $R^1$ and $R^2$ is selected from the group consisting of hydrogen and a hydroxy-protecting group.

2. The compounds of claim 2 where X is a hydroxymethyl group.

3. The compounds of claim 1 where X is a carboxaldehyde group.

4. Compounds having the formula:

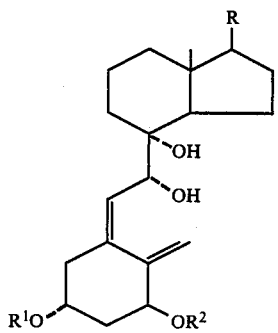

where each of $R^1$ and $R^2$ is selected from hydrogen or a hydroxy-protecting group, and where R is a side-chain having the structure:

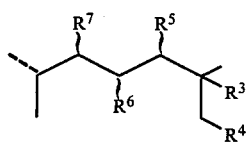

wherein each of $R^3$ and $R^4$ is selected from the group consisting of hydrogen, hydroxy or protected hydroxy, where $R^5$ is selected from the group consisting of hydrogen, alkyl, hydroxy or protected hydroxy, and where $R^6$ and $R^7$ represent, independently, hydrogen, hydroxy or protected hydroxy, or when taken together, form a carbon-carbon double bond.

5. A compound according to claim 4 where R represents the side-chain of cholesterol.

6. A compound according to claim 4 where R represents the side-chain of ergosterol.

7. A process for preparing a compound having the formula

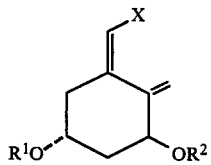

where each of $R^1$ and $R^2$ is selected from the group consisting of hydrogen and an hydroxy-protecting group and where X represents a hydroxy-methyl or a carboxaldehyde group, which comprises treating a 1 alpha-hydroxy-7,8-dihydroxyvitamin D compound having the formula

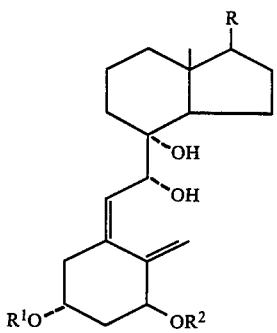

where each of $R^1$ and $R^2$ is selected from the group consisting of hydrogen and an hydroxy-protecting group and where R is a side-chain having the structure

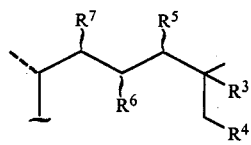

where each of $R^3$ and $R^4$ is selected from the group consisting of hydrogen, hydroxy or protected hydroxy, $R^5$ is selected from the group consisting of hydrogen, hydroxy, alkyl and protected hydroxy, and $R^6$ and $R^7$ independently, represent hydrogen, hydroxy or protected hydroxy, or when taken together form a carbon-carbon double bond, with an oxidative reagent specific to the cleavage of vicinal diols thereby obtaining an aldehyde having the structure

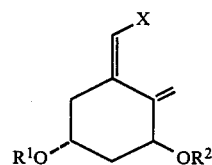

where $R^1$ and $R^2$ have the meaning defined above and X is a carboxaldehyde (—CHO) group and optionally subjecting said aldehyde to reduction with a hydride reducing agent to obtain the corresponding alcohol when X represents an hydroxy methyl group.

* * * * *

Disclaimer 4,755,329.—*Hector F. DeLuca; Heinrich K. Schnoes*, both of Madison, Wisc.; *Seok H. Lee*, Brighton, Mass. PROCESS AND INTERMEDIATES FOR PREPARING 1a-HYDROXYVITAMIN D COMPOUNDS. Patent dated July 5, 1988. Disclaimer filed Feb. 21, 1989, by the assignee, Wisconsin Alumni Research Foundation.

Hereby enters this disclaimer to claims 2 and 3 of said patent.
[ *Official Gazette June 27, 1989* ]